United States Patent [19]

Garabedian

[11] Patent Number: Plant 5,610

[45] Date of Patent: Dec. 24, 1985

[54] PLUM TREE, SOUTHERNER

[76] Inventor: John M. Garabedian, 3104 E. Huntington Blvd., Fresno, Calif. 93702

[21] Appl. No.: 580,258

[22] Filed: Feb. 15, 1984

[51] Int. Cl.[4] ..... A01H 5/00

[52] U.S. Cl. ..... Plt./38

[58] Field of Search ..... Plt./38

*Primary Examiner*—Robert E. Bagwill

*Attorney, Agent, or Firm*—Huebner & Worrel

[57] ABSTRACT

A plum tree substantially as illustrated and described characterized by its bearing fruit which is generally similar to the fruit of the Frontier Plum Tree (unpatented) which ripens at substantially the same time and from which the present variety is distinguished by its more globular shape, deeper red flesh and milder flavor.

1 Drawing Figure

BACKGROUND OF THE NEW VARIETY

For more than five decades, the applicant has engaged in the production and sale of tree fruits of various varieties. These include numerous patented as well as unpatented varieties. Such farming, to be successful, requires the continual improvement of marketable varieties to provide a higher quality product for the consumer and a competitive advantage to the grower.

In an effort continually to upgrade his products, the applicant is continuously on the alert to locate any new varieties that might appear as sports or mutations on the fruit trees of any of his several farms and further has germinated thousands of seeds of peaches, plums and grapes, grown the resultant seedlings to maturity, and carefully studied the characteristics of the progeny. The present variety of plum tree resulted from the latter procedure.

The plum tree of the present invention is noteworthy in the early ripening of its fruit, being ready for harvest by June 25, 1982, and over-ripe by July 15, 1982.

ORIGIN

The present variety of plum tree was a seedling which resulted from the germination by the applicant of numerous drupe seeds at the inventor's ranch at the corner of Church and Greenwood Aves. in Fresno, Calif. in 1968. The parentage of the seedling of the present variety is unknown but the seedling was observed for several years prior to recognition of its desirable characteristics. The applicant asexually reproduced the subject plum tree by grafting scions thereof onto various host trees. The resultant progeny were found to possess the same distinctive characteristics as the original tree. The budded trees were budded and grown on the applicant's ranch at the northwest corner of Belmont and Armstrong Aves., Fresno, Calif.

The specimens of the subject variety plum tree shown in the drawing were first grown in the applicant's nursery Number One, on his Kings Canyon Ranch at 5841 East Kings Canyon, Fresno, Calif.

BRIEF DESCRIPTION OF THE DRAWING

The drawing is a photographic reproduction in color of a twig with leaves of the plum tree of the subject variety, of four whole plums in various attitudes for convenience of observation, of a half of a plum divided on the suture plane, and of a half of a plum divided transversely of the suture plane.

BOTANICAL DESCRIPTION

The following description provides the botanical details of the subject variety plum tree grown under the ecological conditions prevailing in the San Joaquin Valley of California under normal cultural practices. The color definitions are as set forth in Maerz and Paul, *Dictionary of Color,* as follows:

TREE

Size: Medium.
Vigor: Vigorous.
Figure: Upright, spreading, dense, vase-formed.
Productivity: Medium productive.
Regularity of bearing: Regular.
Trunk:
- *Thickness.*—Medium.
- *Texture of bark.*—Medium.

Branches:
- *Thickness.*—Medium.
- *Texture.*—Medium.
- *Color.*—Grayish-Brown, Plate 8-E-10; striations longitudinal: color — light brown to Plate 12-J-6 (Honey Middle 8 Tone +).
- *Lenticels.*—Medium in number; small in size.

Leaves:
- *Shoot.*—Size — Medium; length 10.31±0.78 cm.; width 4.31±0.66 cm.
- *Form.*—Ovate, acuminate, pointed.
- *Thickness.*—Medium.
- *Color.*—Dark green; upper surface Plate 23-C-10; lower surface Plate 22-E-7.
- *Texture.*—Smooth.
- *Marginal form.*—Crenate.
- *Petiole.*—Length — Medium; Thickness — Medium 1.40±0.12 cm.
- *Glands.*—Average number 1.8; opposite; medium; globose, green; positioned at base of blade.
- *Stipules.*—Linear, acute, deutate, tend to absciss.

Spur:
- *Size.*—Medium to small; length 7.57±1.55 cm.; width 2.61±0.44 cm.
- *Form.*—Oval to narrow oval, blunt to acuminate at apex.
- *Thickness.*—Medium.

*Color.*—Dark green; upper surface Plate 23-C-10; lower surface Plate 22-E-7.

*Marginal form.*—Crenate.

*Petiole.*—Length — Medium; Thickness — Medium 1.23±0.42 cm.

*Glands.*—Lacking.

Flower buds: Small, short, obtuse, conic, plump, free, glabrous.

Flowers: Medium, white, Anthers yellow; date of first bloom — Feb. 18, 1983; date of full bloom — Mar. 2, 1983; medium to late compared with other varieties.

FRUIT

Maturity when described: Over-ripe; date — July 15, 1982.

Size: Medium.

*Axial diameter.*—4.86±0.20 cm.

*Diameter transverse in suture plane.*—5.60±0.19 cm.

*Diameter transverse in cheek plane.*—5.82±0.24 cm.

Form: Uniform, oblate, nearly round in transverse section, but slightly compressed toward suture.

*Suture.*—A distinct shallow groove extending from base to apex; ventral edge shorter apically than dorsal edge.

*Ventral surface.*—Rounded, lipped throughout, but less so apically; lips nearly equal.

*Cavity.*—Flaring, slightly elongated in suture plane with suture showing on one side; depth — 0.77±0.34 cm.; breadth — 2.39±0.22 cm.; markings — none.

*Base.*—Broadly rounded.

*Apex.*—Rounded to truncate, slightly depressed at pistil point.

*Pistil point.*—Apical.

Skin: Medium thickness; medium texture; tenacious to flesh; slight tendency to crack.

*Color.*—Dark red, full colored to Plate 56-E-12.

*Down.*—Wanting.

*Bloom.*—Heavy, blue-gray, Plate 38-F-5.

*Dots.*—Usually noticeable, small to medium sized; light brown in color; variable in density from fruit to fruit; more abundant and smaller apically; lacking along suture and in cavity.

Flesh:

*Color.*—Blood red, streaked and mottled with white next to stone; ground color — dull grayish-amber Plate 12-A-5, heavily diffused red from skin to cavity to Plate 55-L-1; surface of pit cavity — dark red.

*Amygdalin.*—Wanting.

*Juice.*—Abundant, moderate.

*Texture.*—Medium, soft, fine, melting.

*Fibers.*—Few, fine, tender.

*Ripening.*—Even.

*Flavor.*—Mild, delicate, sweet.

*Aroma.*—Nearly wanting.

*Eating quality.*—Good.

Stone: Semi-free; adheres to flesh along ventral edges, free on sides toward base; short fibers.

*Size.*—Small, length — 1.93±0.11 cm.; breadth — 1.72±0.06 cm.; thickness — 0.94±0.06 cm.

*Form.*—Broad oval to broad ovate in cheek aspect.

*Base.*—Straight.

*Hilum.*—Narrow, oblong.

*Apex.*—Acuminate.

*Sides.*—Unequal, ventral usually longer and recurved to apical tip.

*Surface.*—Irregularly ridged near base; finely rugose.

*Ventral edge.*—Thin, often a very narrow flange, especially basally; lateral grooves broad, very shallow, inconspicuous; without wing throughout.

*Dorsal edge.*—Full, deep groove throughout.

*Color.*—Light tan, Plate 10-C-3.

*Tendency to split.*—None.

Use: Dessert.

Keeping quality: Good.

Resistance to insects: Medium.

Resistance to disease: Medium.

Shipping quality: Good.

Although the new variety of plum tree possesses the described characteristics as a result of the growing conditions in Fresno County, Calif., in the central part of the San Joaquin Valley, it is to be understood that variations of the usual magnitude in characteristics incident to growing conditions, fertilization, pruning and pest control are to be expected.

Having thus described and illustrated my new variety of plum tree, what I claim as new and desire to secure by Letters Patent is:

1. A new and distinct variety of plum tree, substantially as illustrated and described, characterized by the blood-red flesh of its medium-sized, globular fruit and its general similarity to the Frontier Plum Tree (unpatented) which matures at substantially the same time but from which it is distinguished by its more globular fruit shape, deeper red flesh, and milder flavor.

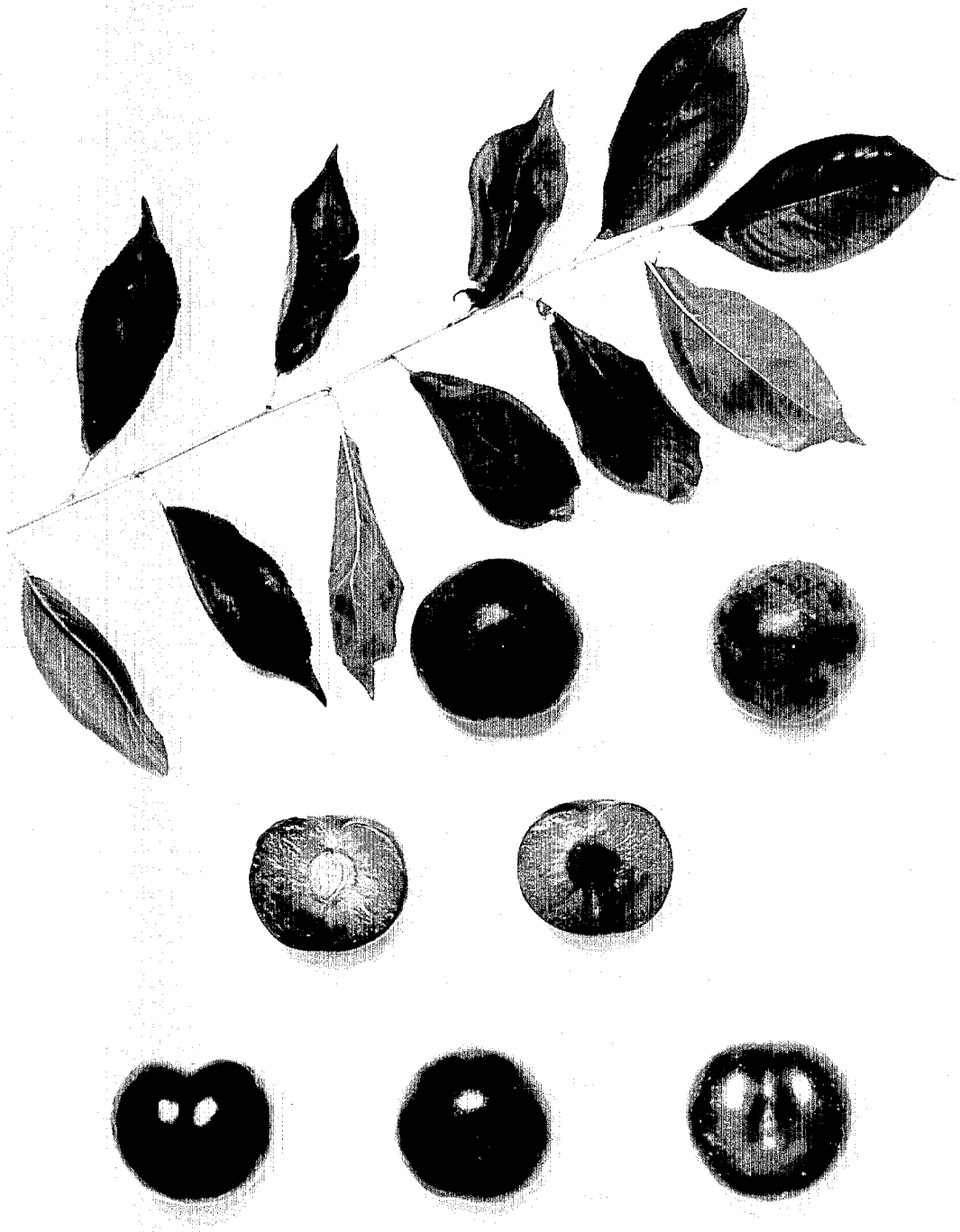

* * * * *